US008805894B2

(12) United States Patent
Valdiserri et al.

(10) Patent No.: US 8,805,894 B2
(45) Date of Patent: Aug. 12, 2014

(54) INTERACTIVE 3-DIMENSIONAL OBJECT-ORIENTED DATABASE INFORMATION STORAGE/RETRIEVAL SYSTEM

(76) Inventors: Michael Valdiserri, Tucson, AZ (US); Warren J. Goble, Tucson, AZ (US)

( * ) Notice: Subject to any disclaimer, the term of this patent is extended or adjusted under 35 U.S.C. 154(b) by 1190 days.

(21) Appl. No.: 10/982,276

(22) Filed: Nov. 5, 2004

(65) Prior Publication Data
US 2006/0101055 A1    May 11, 2006

(51) Int. Cl.
*G06F 17/30* (2006.01)

(52) U.S. Cl.
USPC ........... 707/803; 707/804; 707/805; 382/305; 345/419; 345/679; 345/681

(58) Field of Classification Search
CPC ........... A61B 19/5212; A61B 19/5244; A61B 2019/5289; A61B 2019/5293; A61B 2019/5295
USPC ............. 707/102, 103 R, 731, 803, 804, 805; 382/305; 345/419, 679, 681
See application file for complete search history.

(56) References Cited

U.S. PATENT DOCUMENTS

| | | | |
|---|---|---|---|
| 6,208,974 B1 * | 3/2001 | Campbell et al. | 705/3 |
| 6,463,351 B1 * | 10/2002 | Clynch | 700/163 |
| 6,772,026 B2 * | 8/2004 | Bradbury et al. | 700/98 |
| 6,772,175 B2 * | 8/2004 | MacPherson | 707/104.1 |
| 7,167,864 B1 * | 1/2007 | Vasudevan | 707/10 |
| 7,734,481 B1 * | 6/2010 | Hutton et al. | 705/3 |
| 2004/0068187 A1 * | 4/2004 | Krause et al. | 600/443 |
| 2004/0213877 A1 * | 10/2004 | Badalucca | 426/383 |
| 2005/0251415 A1 * | 11/2005 | Pak | 705/2 |

* cited by examiner

*Primary Examiner* — Hanh Thai
(74) *Attorney, Agent, or Firm* — Greenberg Traurig, LLP

(57) ABSTRACT

An interactive 3-dimensional object-oriented database patient specific information storage system includes an input device, a database containing 3-dimensional meshes of objects each with an object identifier and a symptom list with each symptom having associated ones of the object identifiers of the 3-dimensional meshes of objects. An interface connected to interact with the database and the input device. The interface including a symptom input form for entering symptoms from the symptom list. The interface is designed to select 3-dimensional meshes of objects having ones of object identifiers associated with the entered symptoms and display the selected 3-dimensional meshes of objects on a symptom template. A record of the entered symptoms and the object identifiers of the associated ones of the 3-dimensional meshes of objects is created and stored.

14 Claims, 6 Drawing Sheets

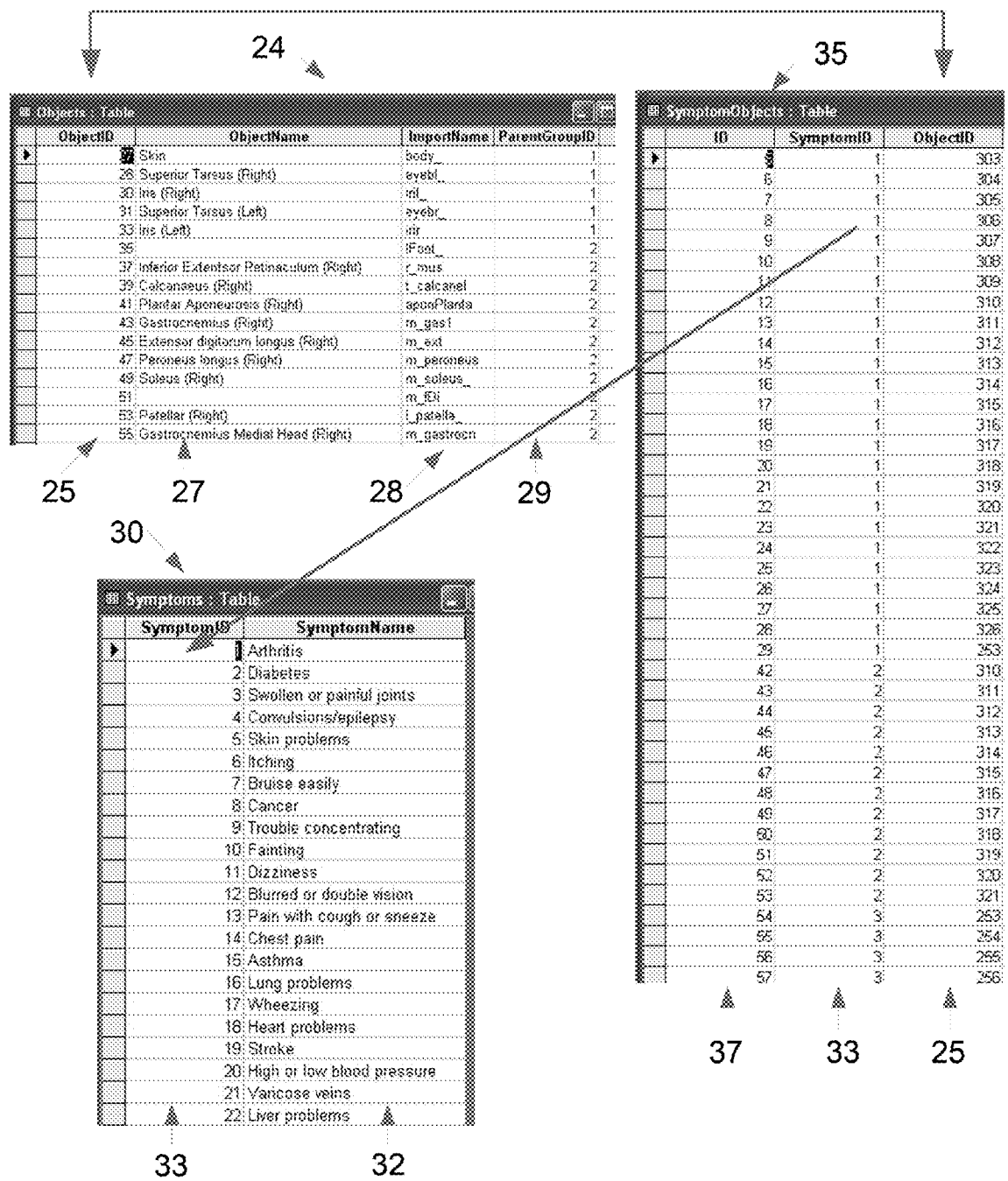
Figure 3 - Objects / Symptoms

Figure 4 - Groups

24

| ObjectID | ObjectName | ImportName | ParentGroupID |
|---|---|---|---|
| 37 | Skin | body_ | 1 |
| 28 | Superior Tarsus (Right) | eyebl_ | 1 |
| 30 | Iris (Right) | iri_ | 1 |
| 31 | Superior Tarsus (Left) | eyebr_ | 1 |
| 33 | Iris (Left) | irir | 1 |
| 35 | | lFoot | 2 |
| 37 | Inferior Extentsor Retinaculum (Right) | r_rods | 2 |
| 39 | Calcanaeus (Right) | t_calcanel | 2 |
| 41 | Plantar Aponeurosis (Right) | aponPlanta | 2 |
| 43 | Gastrocnemius (Right) | m_gas1 | 2 |
| 45 | Extensor digitorum longus (Right) | m_ext | 2 |
| 47 | Peroneus longus (Right) | m_peroneus | 2 |
| 49 | Soleus (Right) | m_soleus_ | 2 |
| 51 | | m_fDi | 2 |
| 53 | Patellar (Right) | l_patella_ | 2 |
| 55 | Gastrocnemius Medial Head (Right) | m_gastrocn | 2 |

25　27　　　　　　　　　　　　28　29

All of these objects are parent group 2; so these objects are Muscles

40

| GroupID | ParentID | GroupName |
|---|---|---|
| 1 | 0 | Skin |
| 2 | 0 | Muscles |
| 3 | 0 | Nerves |
| 4 | 0 | Bones |
| 13 | 4 | Spine |
| 14 | 0 | Lymphatic |
| 15 | 0 | Vascular |
| 16 | 0 | Organs |
| 17 | 0 | Spinal Cord |
| (AutoNumber) | 0 | |

44　45　42

Spine is a child of group "bones" because it's parent is groupID 4 which is bones

| History | |
|---|---|
| First Name: | Last Name: | Middle Initial: F |

Symptoms

| | | |
|---|---|---|
| ☐ Arthritis | ☐ Learning disability | ☐ Menopausal problems |
| ☐ Diabetes | ☐ Stutter | ☐ Breast lumps/discharge |
| ☐ Swollen or painful joints | ☐ Dyslexia | ☐ Bedwetting |
| ☐ Convulsions/Epilepsy | ☐ Mood changes | ☐ Ear infections |
| ☐ Skin problems | ☐ Emotional disorders | ☐ Hepatitis Venereal disease |
| ☐ Itching | ☐ Digestive problems | ☐ AIDS/HIV |
| ☐ Bruise easily | ☐ Excessive gas | ☐ Migranes |
| ☐ Cancer | ☐ Bloating after meals | ☐ Neck pain |
| ☐ Trouble concentrating | ☐ Heartburn | ☐ Numbness, tingling pain in arm |
| ☐ Fainting | ☐ Ulcers | ☐ Jaw pain (TMJ) |
| ☐ Dizziness | ☐ Diarrhea/constipation | ☐ Head seems too heavy |
| ☐ Blurred or double vision | ☐ Colon problems | ☐ Head and shoulders feel tired |
| ☐ Pain with cough or sneeze | ☐ Hemorrhoids | ☐ Shoulder pain |
| ☐ Chest pain | ☐ Prostate problems | ☐ Upper back pain/stiffness |
| ☐ Asthma | ☐ Impotence | ☐ Mid-back pain/stiffness |
| ☐ Lung problems | ☐ Kidney problems | ☑ Low back pain/stiffness |
| ☐ Wheezing | ☐ Light bothers eyes | ☐ Numbness, tingling or pain in b |
| ☐ Heart problems | ☐ Allergies | ☐ Pain with cough, sneeze, or str |
| ☐ Stroke | ☐ Sinus problems | ☐ Hip pain |
| ☐ High or low blood pressure | ☐ Light-headed upon arising | ☐ Foot trouble |
| ☐ Varicose veins | ☐ Stress | ☐ Headaches |
| ☐ Liver problems | ☐ Crave sweets or salts | |
| ☐ Gall bladder problems | ☐ Eating disorders | |
| ☐ Loss of memory | ☐ Trouble sleeping | 72 |
| ☐ Frequent colds/flu | ☐ Kidney stones | |
| ☐ Nervous tension | ☐ Frequent urination | |
| ☐ Irritable | ☐ Painful urination | |
| ☐ Anemia | ☐ Discharge | |
| ☐ Excess sweating | ☐ Menstrual problems | |
| ☐ Tremors | ☐ PMS | |

Surgeries: | Broken bones:

[ Next > ]  Cancel

FIGURE 6

Symptoms
Symptom: Low back pain/stiffness
76
FIGURE 7
Palpation
Muscle:
Cervical 3
Muscle:
Cervical 2
(Axis)
Muscle:
Adductor
Brevis
(Left)
Muscle:
Adductor
Brevis
(Right)
Muscle:
Adductor
Longus
(Left)
Muscle:
Adductor
Longus
(Left)
Muscle:
Adductor
Longus
(Right)
FIGURE 8
Chief Complaint: Low Back Pain
History
ICD9 Codes: E83.7 (Diag) - EXPLOSION, FIRE, OR BURNING IN WATERCRAFT, 2.3 (Diag) - PARATYPHOID FEVER C

INTERACTIVE 3-DIMENSIONAL OBJECT-ORIENTED DATABASE INFORMATION STORAGE/RETRIEVAL SYSTEM

FIELD OF THE INVENTION

This invention relates to information storage/retrieval systems.

More particularly, the present invention relates to information storage/retrieval systems employing 3-dimensional object-oriented databases.

BACKGROUND OF THE INVENTION

The storage of information can be one of the most complex problems or challenges in industry today. In particular, the information must be stored so that it can be easily and efficiently retrieved. Moreover, standardization of physiological measurements are problematic. Generally, this requires the use of key words that can then be searched to find the stored information. In certain or specific areas, such as the medical profession, storage will be according to patients but the information stored can be sketchy, difficult to express, and may it be difficult to reconstruct the specific situation. Complete descriptions of the specific situation and any continuing procedures may be extremely lengthy so that large amounts of storage are required if the description is to be complete and sufficient for later review. Thus, a great amount of time can be expended in describing the situation and the procedures used and each time the stored information is retrieved and reviewed.

Often, information is stored such that only one skilled in the art can understand or decipher the information. In specific instances or applications, it may be desirable for a third party or affected party to view the stored information. For example, doctors, chiropractors or other specialists, often write notes either hard copy or electronic that are very cryptic to a layperson such as a typical patient. The physician must then explain the meaning of the information, often using models or pictures in books. This process can be time consuming and dissatisfying to both parties.

It would be very convenient if descriptions of information to be stored could be simplified, quantified, and standardized to reduce the input time and effort required for storage. It is also desirable to reduce the time and effort required in retrieving and reviewing the stored information and providing information in a form understandable by third parties with minimal assistance from the individual storing the data.

It would be highly advantageous, therefore, to remedy the foregoing and other deficiencies inherent in the prior art.

Accordingly, it is an object of the present invention to provide a new and improved interactive 3-dimensional object-oriented database information storage/retrieval system and method of storage.

Another object of the invention is to provide a new and improved interactive 3-dimensional object database information storage/retrieval system that greatly simplifies storage and retrieval of information.

A further object of the present invention is to provide a new and improved interactive 3-dimensional object database information storage/retrieval system that substantially reduces time and effort for storage and retrieval of information.

SUMMARY OF THE INVENTION

Briefly, to achieve the desired objects of the instant invention in accordance with a preferred embodiment thereof, provided is an interactive 3-dimensional object-oriented database information storage system including an input device, and a database containing 3-dimensional meshes of objects each with an object identifier and stored input selections, each selection having associated object identifiers. An interface is connected to interact with the database and the input device and includes a data input display for receiving input selections. The interface is designed to select 3-dimensional meshes of objects having object identifiers associated with the stored input selections. A record of the input selection and the associated object identifiers is created and stored.

In one embodiment, an interactive 3-dimensional object-oriented database patient information storage system includes an input device, a database containing 3-dimensional meshes of objects each with an object identifier and a symptom list with each symptom having associated ones of the object identifiers of the 3-dimensional meshes of objects. An interface is connected to interact with the database and the input device. The interface including a symptom input form for entering symptoms from the symptom list. The interface is designed to select 3-dimensional meshes of objects having ones of object identifiers associated with the entered symptoms and display the selected 3-dimensional meshes of objects on a symptom template. A record of the entered symptoms and the object identifiers of the associated ones of the 3-dimensional meshes of objects is created and stored.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIGS. 3 and 4 illustrate interacting tables of the database using identifiers for cross-referencing;

FIG. 6 is an information collection form for collecting information of symptoms;

FIG. 7 is a symptom template which displays 3-dimensional object meshes of objects associated with specific symptoms; and FIG. 8 is a template which displays 3-dimensional object meshes of objects that have been palpated.

DETAILED DESCRIPTION OF THE DRAWINGS

Figure 1:
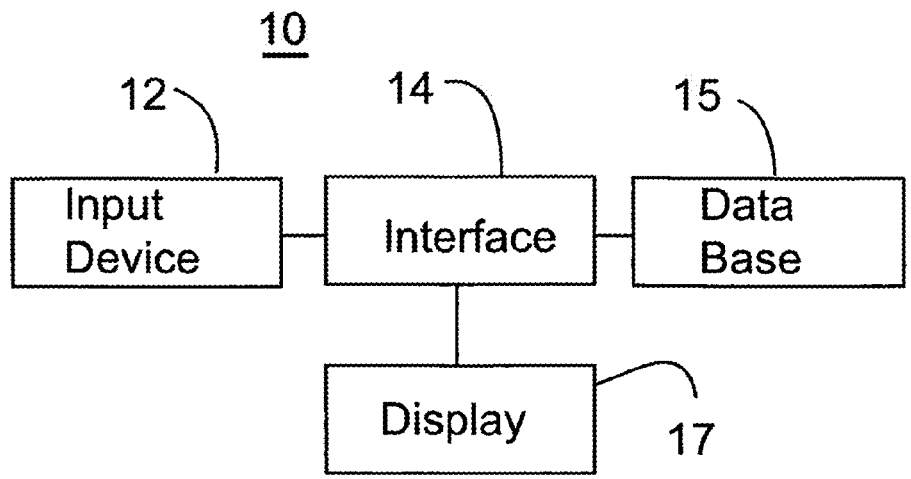
FIG. 1 is a simplified block diagram of an information storage/retrieval system according to the present invention.

Turning now to the drawings in which like reference characters indicate corresponding elements throughout the several views, attention is first directed to FIG. 1, which illustrates a simplified block diagram of an information storage/retrieval system generally designated 10. System 10 includes an input device 12 which can include standard input devices such as a keyboard and mouse or touch screen, but can also include more specialized devices such as medical devices which measure various bodily functions, orientations, etc. The data is received by an interface 14 which interacts with a database 15 containing 3-dimensional meshes of objects with associated identifiers. The 3-dimensional object meshes are stored code of 3-dimensional meshes representing each of the various objects that can be retrieved, displayed, rotated, and otherwise manipulated to illustrate a specific situation or problem. The objects are pieces or parts of any complex assembly or system, such as a human body. Furthermore, since these 3-dimensional object meshes are code, they can be processed or acted upon by algorithms, artificial intelligence algorithms, statistical algorithms, and other cross-referenced data. A 3-dimensional mesh allows representations of 3-dimensional objects to be shown on a 2-dimensional media such as a screen or print-out. A 3-dimensional mesh is constructed of a plurality of vertices. Every vertex is composed of three coordinates x, y, and z. A vertex is defined as three numbers or floating point numbers (meaning decimal points) x, y, and z. A 3-dimensional mesh consists of a number of nth vertices. Vertices are bound together to form faces or polygons which compose the 3-dimensional mesh.

The 3-dimensional object meshes are stored meshes representing different objects of a complex assembly of parts that can be retrieved, displayed, rotated, and otherwise manipulated to illustrate a specific situation or problem. Interface 14 selects 3-dimensional meshes of the objects from database 15 and associates them with the input information or other cross-referenced information. Identifiers for the objects associated with the information are then stored in an associated memory which may be database 15 or other databases in an independent memory device. The stored information can then be displayed or used in the aforementioned algorithms, with the 3-dimensional object meshes from database 15 using the associated identifiers on any desirable media such as a display 17, hard copy print out, or transmitted via a network such as the World Wide Web to remote display devices.

Figure 2:
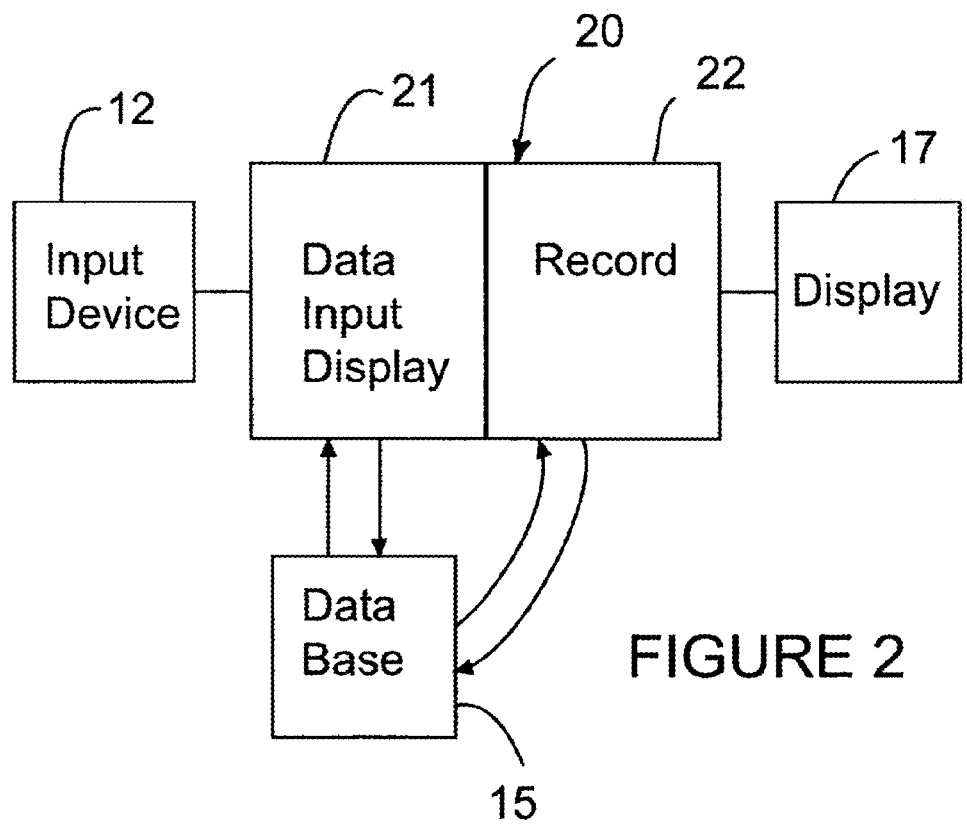
FIG. 2 is a simplified flow chart illustrating the flow of information between components of the information storage/retrieval system of FIG. 1.

In a general example of a process of storing and retrieving information according to the present invention, attention is now directed to FIG. 2. A record 20 can be developed for various applications for complex systems that have been examined, treated/repaired or otherwise manipulated in a manner for which an easily reviewable and updatable history would be desirable. Record 20 includes a data input display 21 and a stored record 22. Input device 12 is employed to retrieve data input display 21 from database 15, which display may include one or more forms and/or templates to be completed and/or manipulated (as will be explained in more detail presently). Requested information is input into data input display 21 using input device 12. The entered data is then associated by interface 14 with objects and 3-dimensional meshes of the objects stored in database 15. Identifiers designate each object and 3-dimensional mesh of the object in database 15. The collected data with associated object identifiers forms a record that can then be stored as stored record 22. Data in stored record 22 can then be displayed in a desired media by retrieving the associated 3-dimensional object mesh of a selected object from database 15 using the identifiers and embedding the 3-dimensional object mesh in the collected data.

With additional reference to FIGS. 3 and 4, an example of the interaction between record 20 and database 15 is illustrated. Database 15 is divided into a collection of tables that include specific items, each item having an identifier. Specifically, table 24 includes objects, each associated with an object identifier 25, an object name 27, an object file name 28 and parent group identifier 29. Object file name 28 permits retrieval of a 3-dimensional mesh file for each specific 3-dimensional object mesh. The collection of tables includes, for example, a symptom table 30 listing a plurality of symptom names 32 each with a corresponding symptom identifier 33. A proprietary symptom cross-reference table 35 cross-references each object identifier 25 with one or more symptom identifiers 33, each cross-reference having a cross-reference identifier 37. In this manner symptom data input in data input display 21 is associated with various objects most likely associated with a problem as indicated by the symptoms.

Referring additionally to FIG. 4, another example of the interaction between record 20 and database 15 is illustrated. In this example, object table 24 is cross-referenced with a group table 40, which includes group names 42 each having an associated group identifier 44. Each group name also includes a parent identifier 45. If the specific group name is a sub-element or subset of another group name, the parent identifier 45 of that specific group name will be the group identifier of the parent group (e.g. the group name 'bones' has group identifier 4, the group name 'spine' has group identifier 13 and parent group identifier 4, indicating it is a subset of group name 'bones').

In table 24, each object name 27 has a parent group identifier 29 which allows cross-referencing with table 40. Parent group identifier 29 of each object 27 of table 24 allows association of that object with a group name 42 of table 40 by matching identifier 29 with group identifier 44. In this manner, 3-dimensional meshes of individual objects can be shown in groups, as defined by table 40. It will be understood by those skilled in the art that there can be any number of objects, and the objects can be divided or categorized into any number of sub-groups and groups to form systems or other logical organization of the objects. Also, the 3-dimensional meshes of the objects can be displayed individually or in any of the sub-groups, groups, etc. in which they are included. The various tables are used only by interface 14 for cross-reference purposes and are not displayed.

Figure 5:
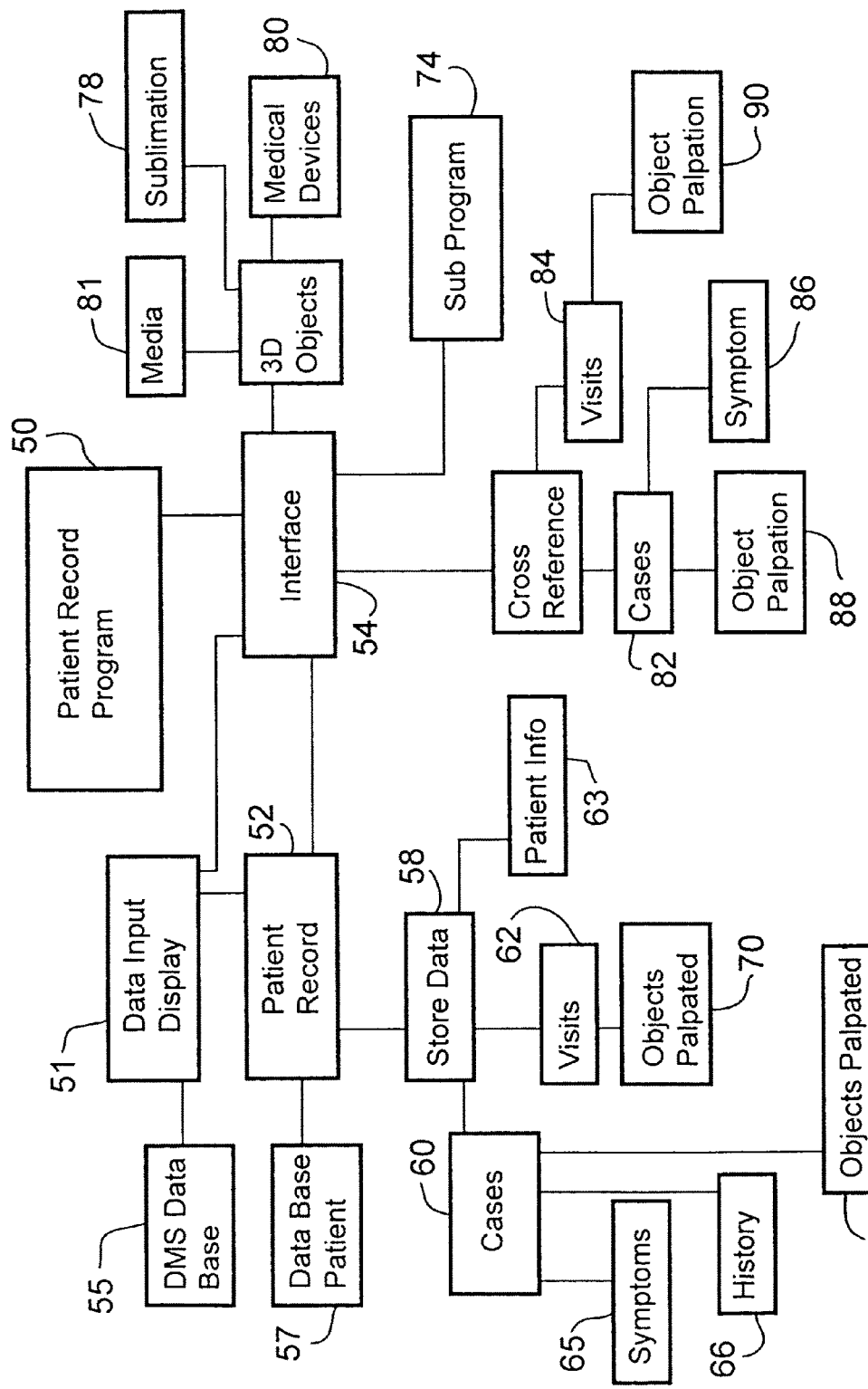
FIG. 5 is a simplified flow/block diagram of a specific application of the information storage/retrieval system of FIG. 1.

Turning now to FIG. 5, a flow/block diagram is illustrated showing the operation of system 10 as used for a specific application. The diagram illustrates the use of a patient record program 50 as a patient record is developed and displayed by system 10. The specific application in this example is for use by a health care provider such as a doctor, chiropractor, and the like. Program 50 coordinates an interface 54 and a database 55 to provide a process flow as will be described presently. In this specific embodiment, database 55 includes a plurality of 3-dimensional object meshes that represent standardized anatomically correct body parts. As a specific example, one or more SQL databases (Microsoft Access Database) can be used. Individual patient records 52 are developed by employing a data input display 51 which display may include one or more forms and/or templates to be completed, those forms and/or templates being drawn from database 55. Information requested by the forms and/or templates is input into the forms and/or templates of data input display 51 using various input devices. Data input display 51 receives patient specific information designating and creating patient record 52. Data in patient record 52 as collected in the forms and/or templates of data input display 51 are stored as patient files in a database, which may be database 55 or one or more separate databases 57.

Data 58 stored in patient record 52 is collected by the forms and/or templates of data input display 51 and can include substantially any data, but in this example include case specific information 60, visit specific information 62, and general patient information 63. An individual patient may have more than one illness or injury, resulting in more than one case. Each visit by a patient may pertain to a previously recorded case or to a partially or completely new case. Prior cases, including symptoms 65, a history 66 of the specific symptoms, and objects palpated 68, are stored in case specific information 60, and any new cases or information pertaining to previously stored cases will be developed and stored through use of the displayed forms and/or templates of data input display 51. Case specific information 60 can include other data as desired, such as postural check, ortho/neuro codes, range of motion and the like. Also, information specific to each visit is developed and stored as visit specific information 62, which also includes any object palpated 70 during that specific visit. As with case specific information 60, visit specific information 62 can include additional data groups such as object palpation, ICD9 codes, CPT codes, selected cases, S.O.A.P. notes, visit information such as description, doctor, dates, and the like. Further, patient history 63 can include basic information on demographics, residential address, billing information, insurance information and the like.

Symptoms 65 of cases 60 are input into patient record 52, for example, by a form 72 of data input display 51. With additional reference to FIG. 6, form 72 is illustrated as a check list of a plurality of possible symptoms. During or after a visit, a health care provider enters the symptom or symptoms of a patient in form 72. Interface 54 cross-references 74 database 55 using identifiers in a manner as described previously with respect to FIGS. 3 and 4, to associate objects and groups or systems to the selected symptoms using a symptom query. As an example, proprietary SQL queries can be employed to find any cross-referenced 3-dimensional object meshes of objects tied to the symptom. The 3-dimensional meshes of the object, objects or groups of objects associated with the symptoms are displayed on a template 76 of FIG. 7. The health care provider can then adjust the objects desired, expand on those shown or otherwise manipulate the object meshes as desired for recording in the patient record. Manipulation can include addition and subtraction of objects meshes, rotation of the object meshes on any axes of a 3-dimensional system, scaling of object meshes and the like. The displayed objects meshes and/or groups and systems of meshes are a starting point for the health care provider, saving time and simplifying the recording process. These object meshes can also be employed as educational aids for the patient or other entities as desired.

The 3-dimensional object meshes stored in database 55 are each oriented to an absolute origin (e.g., absolute 0,0,0 on x, y, and z axes). In this manner, when multiple 3-dimensional object meshes are displayed as a group or system, they are oriented to one another against an absolute origin or reference, establishing a normal. When 3-dimensional object meshes are displayed for specific symptoms in template 76, they reflect a standard, and do not specifically show the patient's body parts. The 3-dimensional object meshes can be manipulated to more closely reflect the patient's true body parts. Referring back to FIG. 5, interface 54 permits each 3-dimensional object meshes to be altered, reflecting the subluxation 78 of that object in a specific patient. Translation data for that object is stored in the patient record to reflect the orientation of the object from normal. Input devices can include medical devices 80 which measure subluxation or any other condition which is desirable to reflect in the records. These readings can be imparted to the 3-dimensional object meshes and stored as data for modifying 3-dimensional object meshes or groups of 3-dimensional object meshes for each patient. Additionally, media 81 can be tied to the 3-dimensional object meshes, stored in the same or separate databases and identifiers for the attached media is entered in the client record. When the 3-dimensional object mesh or meshes are accessed for use in a template, the media file is also accessed and displayed with the object mesh or meshes. For example, a chiropractor may attach a video clip of a therapy to a mesh of an effected group such as the spine. The video clip can be used to educate the patient as to the therapy they have or will undergo. Other media, X-rays, sonograms, pictures, audio, etc. can be employed.

During a subsequent or current visit, patient record program 50, through interface 54, cross-references the current information with information stored relative to prior cases 82 and visits 84 for the specific patient. For example, symptoms 86 indicated during the current visit are automatically cross-referenced to symptoms recorded in prior case so that the health care provider can quickly and easily determine if there are any changes or if the same symptom or symptoms prevail. If new symptoms or a different case is occurring the new symptoms will be stored as a new case in cases 60. Also, any object palpations 88 that were performed in previous cases will appear as templates, shown in FIG. 8. New object palpations deemed necessary by the current symptoms will be performed and added to the stored object palpations 88 in cases 82 and to object palpations 90 in visits 84. It should be understood that 3-dimensional object meshes of the objects (e.g., body areas/parts) palpated are stored using identifiers in a manner as described previously with respect to FIGS. 3 and 4. The entry of new information occurs through data input display 51. Displaying stored records or comparing new records to stored records involves interface 54 cross-referencing cases 82 and visits 84. In other words, the cross-referenced data is linked to a case or visit and further linked to a symptom or object palpation. The symptom or object palpation is then linked to the associated 3-dimensional object mesh.

The forms and templates of data input display 51, whether those displaying newly entered data or those showing previously entered data, are preferably dynamic interactive forms/templates having embedded windows which contain the associated 3-dimensional object meshes or groups of object meshes. The dynamic aspect allows the object meshes to be manipulated as previously described, directly on the form/template and printed, saved, displayed, etc. as desired. The dynamic feature can be accomplished by generating forms/templates in HTML for standardization issues. This will provide the ability to print and save these records and also will have limited functionality within the medical forms/templates, such as rotation, pan, zoom, groups, selection, move, and rotate. By using MSHTML technologies, the patient record can be edited before saving or printing. MSHTML has a sub-system interface called "Rendering Behavior", allowing developers to render their own graphics within an HTML element. MSHTML is a Microsoft COM technology used to display and edit HTML in the preferred embodiment.

Thus an interactive 3-dimensional object-oriented database information storage/retrieval system and method of storage has been disclosed. The interactive 3-dimensional object-oriented database information storage/retrieval system greatly simplifies storage and retrieval of information, substantially reduces time and effort for storage and retrieval of information, and allows a variety of algorithmic operations to be preformed on the databased information, including the 3-dimensional object meshes.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An interactive 3-dimensional object-oriented database information storage system comprising:
an input device;
a database containing 3-dimensional meshes of objects comprising a plurality of anatomically correct representations of human body parts of a patient, each objects with an object identifier and stored input selections;
an interface connected to interact with the database and the input device, the interface including a data input display comprising a checklist of a plurality of possible symptoms for receiving input selections of symptoms from a patient or healthcare provider;
the interface designed to select 3-dimensional meshes of objects comprising the plurality of anatomically correct representations of human body parts having object identifiers associated with the stored input selections and display the selected 3-dimensional meshes of objects in a form/template to enable graphical navigation and selection of anatomically correct human body parts; and
the form/template is dynamically interactive, allowing manipulation of the selected 3-dimensional meshes of objects comprising the plurality of anatomically correct representations of human body parts, wherein the manipulation comprises adding 3-dimensional meshes of objects comprising additional anatomically correct representations of human body parts based at least in part on at least one symptom provided by the patient, subtracting at least a portion of the 3-dimensional meshes of objects comprising anatomically correct representations of human body parts, and orienting at least a portion of the 3-dimensional meshes of objects comprising the plurality of anatomically correct representations of human body parts relative to an absolute origin.

2. The system as claimed in claim 1, wherein the data input display includes a plurality of forms/templates each of which are configured and arranged to be displayed individually.

3. The system as claimed in claim 1, wherein the 3-dimensional meshes of objects comprising the plurality of anatomically correct representations of human body parts are each oriented to the absolute origin and are configured and arranged to be manipulated around an X, Y and Z axes.

4. The system as claimed in claim 3, wherein a record of the input selection and the associated object identifiers is created and stored, and translational data of the selected 3-dimensional meshes of objects comprising the plurality of anatomically correct representations of human body parts are included in the record for translating the selected 3-dimensional meshes of objects from the absolute origin allowing for a variance between the position of the selected 3-dimensional meshes of objects and the absolute origin to be calculated.

5. The system as claimed in claim 1, wherein the interface is further designed to select a group of the 3-dimensional meshes of objects comprising the plurality of anatomically correct representations of human body parts having object identifiers associated with the stored input selections, and group identifiers matching the group.

6. An interactive 3-dimensional object-oriented database patient information storage system comprising:
an input device;
a database containing 3-dimensional meshes of objects comprising a plurality of anatomically correct representations of human body parts of a patient each objects with an object identifier, and a symptom list provided by a patient with each symptom having associated object identifiers of the 3-dimensional meshes of objects comprising the plurality of anatomically correct representations of human body parts;
an interface connected to interact with the database and the input device, the interface including a symptom input form comprising a plurality of possible symptoms for receiving input selections of symptoms from a patient and for entering symptoms provided by the patient or a healthcare provider from the symptom list,
the interface designed to select 3-dimensional meshes of objects comprising the plurality of anatomically correct representations of human body parts having object identifiers associated with at least one symptom from the patient or the healthcare provider and display the selected 3-dimensional meshes of objects on a symptom template, the symptom template being dynamically interactive, and the interface configured to enable a user to manipulate the selected 3-dimensional meshes of objects comprising the plurality of anatomically correct representations of human body parts,
and wherein the manipulation comprises adding 3-dimensional meshes of objects comprising additional anatomically correct representations of human body parts independently or at least partially based on at least one symptom provided by the patient or healthcare provider, subtracting or adding at least a portion of the 3-dimensional meshes of objects individually or in groups comprising anatomically correct representations of human body parts independently or in groups at least partially based on the entered symptoms, and orienting at least a portion of the 3-dimensional meshes of objects comprising the plurality of anatomically correct representations of human body parts relative to an absolute origin.

7. The system as claimed in claim 6, wherein the data input display includes additional forms/templates each of which are configured and arranged to be displayed individually.

8. The system as claimed in claim 6, wherein the 3-dimensional meshes of objects comprising the plurality of anatomically correct representations of human body parts are each oriented to the absolute origin and are configured and arranged to be manipulated around 3 axes.

9. The system as claimed in claim 8, wherein a record of the entered symptoms and the object identifiers of the associated ones of the 3-dimensional meshes of objects comprising the plurality of anatomically correct representations of human body parts is created and stored and translational data of selected 3-dimensional meshes of objects are included in the record for translating the selected 3-dimensional meshes of objects comprising the plurality of anatomically correct representations of human body parts from the absolute origin.

10. The system as claimed in claim 6, wherein the interface is further designed to select a group of the 3-dimensional meshes of objects having ones of object identifiers associated with the entered symptoms, and group identifiers matching the group.

11. The system as claimed in claim 6, wherein the 3-dimensional object meshes comprising the plurality of anatomically correct representations of human body parts are code that configured and arranged to be processed or acted upon by algorithms, artificial intelligence algorithms, statistical algorithms, and other cross-referenced data comprising calculations of position deviations at points in time.

12. A patient information storage system comprising:
at least one database configured and arranged for being in communication with at least one medical device, the at least one database being configured and arranged for receiving medical data from the at least one medical device; and
an interface being configured and arranged for interacting with the at least one database and the at least one medical device, the interface being configured to impart at least a portion of the medical data onto 3-dimensional meshes of objects comprising a plurality of anatomically correct representations of human body parts of a patient and to store the 3-dimensional meshes of objects comprising the plurality of anatomically correct representations of human body parts as code within the at least one database, wherein the interface is configured and arranged for organizing the stored medical data imparted onto the 3-dimensional meshes of objects comprising the plurality of anatomically correct representations of human body parts in at least one of a patient-specific directory, a visit-specific directory, and a case-specific directory, and accessing the stored medical data imparted onto the 3-dimensional meshes of objects comprising the plurality of anatomically correct representations of human body parts and manipulating the stored 3-dimensional meshes of objects comprising the plurality of anatomically correct representations of human body parts individually or in response to at least one symptom provided by the patient or a healthcare provider from a check list of a plurality of possible symptoms provided to the patient.

13. The patient information storage system of claim 12, wherein the interface is configured and arranged to cross-reference the additional medical data with the stored medical data imparted onto the 3-dimensional meshes of objects comprising the plurality of anatomically correct representations of human body parts.

14. The patient information storage system of claim 12, wherein the manipulating comprises adding additional 3-dimensional meshes of objects comprising additional anatomically correct representations of human body parts independently or based at least on part on at least one symptom provided by the patient or healthcare provider, subtracting at least a portion of the 3-dimensional meshes of objects comprising anatomically correct representations of human body parts based at least on part on at least one symptom provided by the patient, and orienting at least a portion of the 3-dimensional meshes of objects comprising the plurality of anatomically correct representations of human body parts relative to an absolute origin.

* * * * *